United States Patent [19]

Boyles et al.

[11] 4,415,350

[45] Nov. 15, 1983

[54] AUXIN COMPOSITIONS OF PHENYL THIOESTERS OF INDOLE-3-ALKANOIC ACIDS AND THEIR USE AS AUXIN GROWTH REGULATORS

[75] Inventors: David A. Boyles; Jack R. Gaines, both of Rapid City, S. Dak.; Bruce E. Haissig, Rhinelander, Wis.

[73] Assignee: The United States of America as represented by the Department of Agriculture, Washington, D.C.

[21] Appl. No.: 367,638

[22] Filed: Apr. 12, 1982

[51] Int. Cl.$^3$ .................... A01N 43/38; C07D 209/18
[52] U.S. Cl. ........................................ 71/77; 548/494
[58] Field of Search ............................ 548/494; 71/77

[56] References Cited

U.S. PATENT DOCUMENTS 4,297,125  10/1981  Haissig et al. ................. 598/494 X Primary Examiner—Nicholas S. Rizzo
Assistant Examiner—D. B. Springer
Attorney, Agent, or Firm—M. Howard Silverstein; David G. McConnell

[57] ABSTRACT

Aryl esters and thioesters of indole-3-alkanoic acids, such as indole-3-acetaic acid and indole-3-butyric acid, are prepared by chemical reaction of the acid with a phenol, substituted phenol, or thiophenol in a tertiary amine solvent. A phosphorus or sulfur halide in a suitable solvent is added dropwise to the cold amine solution. The reaction produced is separated and purified by standard methods. Phenyl-indole-3-thiolobutyrate as well as other aryl esters of indole-3-alkanoic acids is effective as an auxin plant growth regulator and adventitious root initiator.

4 Claims, No Drawings

AUXIN COMPOSITIONS OF PHENYL THIOESTERS OF INDOLE-3-ALKANOIC ACIDS AND THEIR USE AS AUXIN GROWTH REGULATORS

FIELD OF THE INVENTION

The invention herein relates to a novel process for preparing aryl esters and thioesters of Indole-3-alkanoic acids and their use as synthetic plant growth hormones.

CROSS REFERENCE TO RELATED APPLICATIONS

The disclosure in the instant application is related to that set forth in the allowed U.S. patent application to Haissig et al., Ser. No. 052,656, filed June 27, 1979 and entitled "Improved Tree Rooting Using Synthetic Auxins", the disclosure of which is incorporated herein by reference.*

*Also incorporated by reference is a companion case Ser. No. 367,639, filed Apr. 12, 1982, entitled "Novel Synthesis of N-Phenyl and N-Substituted Phenyl Indolyl-3-Acetamide and Indolyl-3-Butyramide and Related Esters and Thioesters and Their Use as Auxin Growth Regulators".

BACKGROUND OF THE INVENTION

Naturally occurring auxins, which are plant hormones which, in minute quantities, act to promote or modify plant growth as in root and bud formation, are known. Such compositions include indole-3-acetic acid (hereinafter denoted IAA) which is known to stimulate adventitious root formation in cuttings of the easy-to-root plants, otherwise known as "good rooters" (Went et al. 1937, Phytohormones, Mac Millan Co., N.Y., page 294). Synthetically prepared auxins such as indole-3-butyric acid (IBA) and Naphthalene-acetic acid (NAA) have more effectively induced rooting in cuttings, particularly cuttings of difficult-to-root species, otherwise known as "poor rooters" (Audus, 1959, Plant Growth Substances, 2nd edition, Interscience Publications Inc., N.Y., page 553; also see Hartmann and Kester, 1975, Plant Propagation, 3rd Edition, Prentice-Hall, Inc., Englewood Cliffs, N.J.).

Simple phenols when administered in admixture with an auxin sometimes cause a synergistic response in adventitious root initiation (Haissig, 1974, Influences of auxins and auxin synergists on adventitious root primordium initiation and development, New Zealand Journal of Forestry Science 4(2): 311–323; also Gorter, Physiol. Plant. 1962, 15: 88 to 95). Several theories have been proposed to explain the synergism, one theory being that auxin molecules become bonded to the phenolic moiety and that the conjugated composition induces root initiation more effectively than either the auxin or the phenolic compound individually.

Methyl or ethyl esters of auxins have sometimes been shown to enhance adventitious root initiation more effectively than the corresponding free acids (Veldstra, 1944, Researches on Plant Growth Substances, Enzymologia II, pp. 97–163). The naturally occurring auxin IAA at times appears naturally esterified to form other compounds, and poorly defined auxin phenolic conjugates have been reported (Schantz, 1966, Chemistry of naturally occurring growth regulating substances, Ann. Rev. Plant Physiology, 17: 409–438).

A U.S. patent to Grace, U.S. Pat. No. 2,204,213 discloses the use of indole-3-acetic acid, indole-butyric acid, α naphthyl acetic acid, phenyl-acetic acid, indolepropionic acid and the salts and esters thereof as auxins or plant hormones for stimulating seed germination and plant growth therefrom of wheat, barley, soya bean and tomato seeds.

Among the known auxins, IAA does not appear to work effectively as a rooting hormone on woody as opposed to herbaceous cuttings. All commercially available rooting hormone prepartions comprise IBA, NAA, amides of naphthalene-acetic acid, mixtures of the foregoing, or mixtures of the foregoing with IAA. These synthetic auxin preparations have been available for many years but are generally unsatisfactory as plant hormone root initiators for "poor rooters" and "non-rooters" and, until the inventions disclosed in said Ser. No. 052,656, no more effective preparations have appeared over the years despite the need for more effective plant rooting hormones (New Vistas in Plant Propagation, International Plant Propagators Society Combined Proceedings, 1977, 27: 106–113).

It has been reported that phenyl-indole-3-acetate (P-IAA) produced 2 to 4 times as many root primordia per leafy bean cutting (Top Crop), an herbaceous plant, as did IAA (Haissig, 1978, Influence of phenyl indole-3-acetate on adventitious root primordium initiation and development, Plant Physiology (Supplement) 61 (4): 65).

A logical applied compound to enhance root primordium initiation (other than mixtures of auxins and phenolics, as described above) would appear to comprise a molecule resulting from a carboxylic acid-phenol esterification reaction, or an analogue or derivative thereof. Synthesis of such esters as phenyl indole-3-butyrate and 3-hydroxyphenyl indole-3-acetate has been attempted (Nekuda, 1976, Synthesis of derivatives of indole-3-acetic acid, M.S. Thesis, South Dakota School of Mines and Technology; Giacoletto, 1978, Synthesis of derivatives of indole-3-acetic acid, M.S. Thesis, South Dakota School of Mines and Technology). The Nekuda and Giacoletto MS theses are both incorporated herein by reference. Testing the aforementioned aryl esters on bean (*Phaseolus vulgaris* cv. Top Crop) cuttings proved that phenyl and 3-hydroxyphenyl indole-3-acetate are ten or more times as effective, on a molar basis, as compared with indole-3-acetic acid. These esters had no effect on jack pine (*Pinus banksiana* Lamb) cuttings because only more active synthetic auxins, such as indole-3-butyric acid (IBA) and naphthalene acetic acid (NAA), usually induce primordium root initiation in woody plant cuttings, to any substantial degree (Haissig, 1979, Influence of aryl esters of indole-3-acetic and indole-3-butyric acids on adventitious root primordium initiation and development, Physiologia Plantarum 47: 29–33).

Phenyl indole-3-butyrate, however, yielded more rooted jack pine cuttings than did indole-3-butyric acid treatment. It was therefore concluded that certain aryl esters may be synthesized that are more effective in inducing adventitious root initiation than other phenyl or 3-hydroxyphenyl esters and than other aryl esters of non-indole auxins, such as naphthalene-acetic acid (Haissig et al. patent application Ser. No. 052,656, referred to above).

The development of new synthetic procedures for preparing new auxins or plant growth regulators is discussed in an article published in 1980; see Boyles M.S. thesis, South Dakota School Mines and Technology. This Boyles M.S. thesis is likewise incorporated herein by reference.

SUMMARY AND OBJECTS OF THE INVENTION

The invention herein concerns a novel chemical procedure for preparing aryl esters and thioesters of indole-3-acetic acid and indole-3-butyric acid in higher yield and purity than has previously been achieved; and novel rooting hormone compositions including derivative esters of the aforementioned acids.

An object of the invention is to use such aryl esters as improved synthetic auxins, or plant hormones, for achieving more effective adventitious root initiation.

It is another object of the invention to overcome the deficiencies in the prior art, which have been extensively discussed above, with a view to more effectively induce rooting in difficult-to-root plant species, including trees.

It is yet another object to provide for the economic propagation of woody plants, including trees.

A further object is to provide a process for making improved synthetic auxins.

These and other objects of the invention are achieved by the improved synthesis of phenyl indole-3-butyrate and phenyl indole-3-acetate, their analogues, and the 4-chlorophenyl and 2,4,6-tribromophenyl derivatives of the above-mentioned esters, and the novel use as rooting hormones of such derivatives and analogues. The above objects were further achieved by the synthesis and testing, as rooting hormones, of the thioesters of the above compounds by using thiophenol as a substitute reagent to synthesize the phenol moiety of the ester.

DETAILED DESCRIPTION OF PREFERRED EMBODIMENTS

Among the esterification processes mentioned in the Nekuda paper, supra, were those utilizing mixed anhydrides and acid chlorides, neither of which were acceptable for the esterification of indole alkanoic acids. Nekuda, therefore, investigated the use of dicyclohexylcarbodiimide as a reagent, in such an esterification reaction. This reagent is known to be effective in peptide synthesis reactions (Fox et al. 1957, Introduction to Protein Chemistry, John Wiley & Sons, Inc. N.Y. pp. 169–170). Giacoletto (see paper supra) used dicyclohexylcarbodiimide as a reagent to produce a physiologically effective yield (17%) of phenyl indole-3-butyrate. In the dicyclohexylcarbodiimide esterification process it is difficult to separate the fluffy dicyclohexylurea needles, which are produced from the sticky ethereal solution of the ester reaction product. Any solvent used to liberate the ester inherently functions to dissolve the dicyclohexylurea needles, which mandates repetitious crystallizations and filtrations (which normally exceeds five cycles of such procedure). There is no way, known to the prior art, to circumvent these difficulties. In the Giacoletto process, mentioned supra, similar difficulties were encountered in attempting to produce the halogenated derivatives of the phenyl indole esters.

In order to overcome the above problems, new methods have been developed to produce aryl esters of indole-3-acetic and indole-3-butyric acids in purer form and in higher yields than has hitherto been accomplished.

Applicants' novel esterification process, as more fully described in the example below, was developed particularly for synthesizing phenyl esters of indolealkanoic acids and attained the objectives indicated above.

EXAMPLE 1

Initially, 0.025 moles or 5.018 grams of indole-3-butyric acid and 0.0275 mol or 2.588 g of phenol were dissolved in 25 ml of pyridine and the solution was cooled. Next, 0.032 mol or 3.03 ml of phosphorus oxychloride was added to 20 ml of methylene chloride to form a solution. This solution was then added dropwise to the cold pyridine solution, while stirring. Stirring was continued for a short time after the dropwise addition had been completed. The product was separated and purified by standard methods. The ester reaction product was chemically and physically identified by determining its melting point to be 72° C. using a Fisher-Johns melting point apparatus and by obtaining infrared spectra using a Beckman, Model IR-10, double beam spectrophotometer. Solid samples of the ester were dispersed in a potassium bromide matrix while liquid samples of the ester were spread on silver chloride plates. The scan speed of the spectrophotometer was 14 minutes. Quantitative carbon, hydrogen and nitrogen determinations were made on the ester by Galbraith Laboratories, located in Knoxville, Tenn. The ester reaction product, described above, was thus chemically identified to be phenyl indole-3-butyrate and was recovered in a yield calculated to be 91 percent.

In the above example, instead of pyridine, other tertiary amines can be used. Also, instead of phosphorus oxychloride mentioned above, $PCl_3$, $PCl_5$, $PBr_3$, $PBr_5$, $POBr_3$, $SOBr_2$, $SOCl_2$, or similar reagents can be used successfully. Moreover, instead of methylene chloride mentioned above, other solvents of similar solvent capability can be used successfully.

EXAMPLE 2

Phenyl indole-3-acetate was recovered and identified, in similar fashion, by following the procedure set forth above in Example 1 except that 0.0250 moles of indole-3-acetic acid was substituted for the indole-3-butyric acid reactant of Example 1.

EXAMPLE 3

The ester 4-chlorophenyl indole-3-butyrate was recovered and identified in similar fashion by following the procedure set forth above in Example 1 except that 0.0275 moles of 4-chlorophenol was substituted for the phenol reactant of Example 1.

EXAMPLE 4

4-chlorophenyl indole-3-acetate was recovered and identified by following the procedure set forth above in example 2 except that 0.0275 moles of 4-chlorophenol was substituted for the phenol reactant of Example 2.

EXAMPLE 5

Similarly, recovery and chemical identification of the ester 2,4,6-tribromophenyl indole-3-butyrate was effected by following the procedure outlined above in Example 1 except that 0.0275 moles of 2,4,6-tribromophenol was substituted for the phenol reactant of Example 1.

EXAMPLE 6

Phenyl indole-3-thioloacetate was similarily recovered and chemically identified by following the procedure of Example 2 except that 0.0275 mole of thiophenol was substituted for the phenol reactant of Example 2.

EXAMPLE 7

Phenyl indole-3-thiolobutyrate was recovered and chemically identified by following the procedure of Example 1 except that 0.0275 mole of thiophenol was substituted for the phenol reactant of Example 1.

Other aryl esters of indole-3-alkanoic acids were similarly synthesized and include 2,4-dichlorophenyl indole-3-butyrate; 2,4,6,-tribromophenyl indole-3-acetate; 4-carbethoxyphenyl indole-3-acetate; 4-carbethoxyphenyl indole-3-butyrate; 4-(carbomethoxyvinylenephenyl) indole-3-acetate; 4-(carbomethoxyvinylenephenyl) indole-3-butyrate; 4-(carbomethoxyvinylene-2,6-dimethoxyphenyl) indole-3-acetate and 4-(carbomethoxyvinylene-2,6-dimethoxyphenyl) indole-3-butyrate.

BIOASSAYS OF THE ABOVE ESTERS

Bioassay of activity of the above ester products was done in rooting trials with bean (*Phaseolus vulgaris* cv. Top Crop) or jack pine (*Pinus banksiana* Lamb.) cuttings, or with both, as previously described above (Haissig article published 1979).

Current evidence indicates that auxin growth regulating compounds of the types dealt with in this research must be structurally intact at the time that plant tissues are treated but that enzymic hydrolysis occurs in plant tissues. Hydrolysis after entry into cells apparently yields the free active auxin. By extension, these new auxin growth regulators seem to be more effective than the parent compounds because of, for example, greater cellular uptake.

It is sometimes desirable to control tests of new compounds with individual hydrolysis products and their mixtures in order to establish which compounds are responsible for the physiological response, if any. In these trials, the new compound was compared with the parent auxin, and sometimes with the probable products that would result from the new compound by enzymic hydrolysis.

The ability of a compound to enhance adventitious root primordium initiation has been a classical test of auxin activity. In tests with bean and jack pine, phenyl indole-3-thiolobutyrate (P-ITB) was as or more effective in inducing adventitious root initiation than indole-3-butyric acid (IBA). Thus, phenyl indole-3-thiolobutyrate is a potent auxin, and structurally unique.

Of the previously known indole auxins, IBA has been very potent, particularly for induction of adventitious root initiation in both herbaceous and woody plants. The activity of IBA has now been exceeded by phenyl indole-3-butyrate or equalled or exceeded by phenyl indole-3-thiolobutyrate, each of which have been synthesized by practicing the new chemical process described supra.

The question naturally arises as to why no phenolic esters of indolealkanoic acids have been synthesized, especially if one considers the proliferation of indolic derivatives recorded in the chemical literature. Some indolic derivatives have been synthesized and tested as compounds of actual and potential auxin activity, including various alkyl esters of indolealkanoic acids. Phenol has been used as a synergist with various auxins with positive results; see Gorter, Physiol. Plant. 1962, 15: 88 to 95, mentioned supra.

In view of the ubiquity of phenolics in plant metabolism, it is logical that phenolic esters of indolealkanoic acids might also possess auxin activity. That such compounds have not been previously synthesized can only attest to the difficulty which their synthesis presents to the chemist.

As mentioned by Haissig, Gaines, and Giacoletto in allowed patent application Ser. No. 052,656 referred to supra, the classical routes of esterification (Fischer, acid chloride, and acid anhydride methods) do not work with the highly acid-sensitive indole auxins. Although dicyclohexylcarbodiimide is successful, the difficulty in work-up and resulting low yield make the method inefficient and commercially impractical in view of the expense of the starting materials.

On the contrary, our novel method disclosed herein produces a superior product, both in quality and yield.

Our method as described above is unique and unequaled in its production of, for example, phenyl indole-3-butyrate and its analogues and derivatives, because of simplicity, ease of product isolation, and superior yield.

The table below includes test data that demonstrates the effect of phenyl indole-3-thiolobutyrate on adventitious root initiation and development in bean cuttings. Data are means based on 100 values from two replications of the experiment in time. An asterisk in the column below a mean indicates that the mean below which the asterisk appears differed significantly (Pr>0.05) from the treatment mean in the row where the asterisk appears. Statistical comparisons are based on a Mann-Whitney U-test.

TABLE 1

| Treatment | | Conc | No. primordia per cutting by treatment no. | | | | | | | | |
|---|---|---|---|---|---|---|---|---|---|---|---|
| No. | Name | (μmol/l) | (1) | (2) | (3) | (4) | (5) | (6) | (7) | (8) | (9) |
| (1) | Control | | 10.0 | | | | | | | | |
| (2) | TP | 0.2 | | 10.4 | | | | | | | |
| (3) | TP | 2.0 | * | | 11.9 | | | | | | |
| (4) | IBA | 0.2 | * | * | * | 17.9 | | | | | |
| (5) | IBA | 2.0 | * | * | * | * | 32.7 | | | | |
| (6) | TP + IBA | 0.2 each | * | * | * | | * | 17.0 | | | |
| (7) | TP + IBA | 2.0 each | * | * | * | * | * | * | 29.1 | | |
| (8) | P-ITB | 0.2 | * | * | * | | * | | * | 17.7 | |
| (9) | P-ITB | 2.0 | * | * | * | * | | * | * | * | 35.0 |

| Treatment | | Conc | No. roots per cutting by treatment no. | | | | | | | | |
|---|---|---|---|---|---|---|---|---|---|---|---|
| No. | Name | (μmol/l) | (1) | (2) | (3) | (4) | (5) | (6) | (7) | (8) | (9) |
| (1) | Control | | 3.4 | | | | | | | | |
| (2) | TP | 0.2 | | 4.9 | | | | | | | |
| (3) | TP | 2.0 | * | | 2.7 | | | | | | |
| (4) | IBA | 0.2 | | | * | 5.0 | | | | | |
| (5) | IBA | 2.0 | * | * | * | * | 14.0 | | | | |
| (6) | TP + IBA | 0.2 each | | | * | | * | 3.8 | | | |

TABLE 1-continued

| | | | | | | | | | | | |
|---|---|---|---|---|---|---|---|---|---|---|---|
| (7) | TP + IBA | 2.0 each | * | * | * | * | * | * | 6.3 | | |
| (8) | P-ITB | 0.2 | | | * | | * | * | | 6.5 | |
| (9) | P-ITB | 2.0 | * | * | * | * | | * | * | * | 11.5 |

Abbreviations:
TP—thiophenol;
IBA—indole-3-butyric acid
P-ITB—phenyl indole-3-thiolobutyrate Tests with bean cuttings indicated that the high (2.0 μmol/l) concentration of indole-3-butyric acid (IBA) and phenyl indole-3-thiolobutyrate (P-ITB) treatments induced equal amounts of primordia and elongated roots, which exceeded the control or any other treatment at both concentrations that were tested (Table I). At 2.0 μmol/l, P-ITB treatment produced significantly more roots and elongated roots per cutting than did a mixture of 2.0 μmol/l thiophenol and 2.0 μmol/l IBA (Table I).

At a lower concentration tested (0.2 μmol/l), IBA, P-ITB, and the mixture of IBA and thiophenol yielded equal numbers of primordia per cutting. At 0.2 μmol/l, no treatment yielded more elongated roots than the control treatment.

The root-inducing and phytotoxic effects of P-ITB treatment, in comparison with no (control) or IBA treatment, were also tested (Table 2). Jack pine seedling cuttings were the test material. The results showed that, under the conditions of this test, P-ITB treatment resulted in more roots per cutting, longer roots per cuttings, and a greater number of rooted cuttings than either the control or IBA treatment (Table 2). IBA treatment was not greater than the control for any these three types of data (Table 2). In addition, P-ITB treatment was much less phytotoxic than IBA treatment. IBA treatment resulted in 85% of cuttings with dead basal stems, in comparison with none for either control of P-ITB treatment (Table 2).

Phenyl indole-3-butyrate and phenyl indole-3-acetate have been previously tested for their effect on adventitious root initiation and development on jack pine and bean cuttings, respectively; see data in Tables in specification of the above-mentioned allowed Haissig et al. patent application, Ser. No. 052,656 and in the article published by Haissig in 1979, also mentioned above.

From the foregoing disclosure, the following conclusions may be drawn:

1. The sensitive nature of the compounds indicated in this disclosure and the expense of indolealkanoic reagents have dictated the development of unique and high-yielding methods for the synthesis of new auxins, such as by the novel method described above, so that the use of the auxin can become a commercial reality.

2. The method that is disclosed herein produces phenyl indole-3-butyrate, phenyl indole-3-acetate, substituted phenyl esters of indolealkanoic acids, and thioesters of indolealkanoic acids in excellent yield and quality, as set forth above.

3. The method has been used to synthesize auxin growth regulators that have proven to be as effective or more effective than indole-3-butyric acid in promoting the initiation of adventitious roots. These improved auxin compounds are phenyl indole-3-butyrate and phenyl indole-3-thiolobutyrate. Physiological auxin activity of phenyl indole-3-butyrate was previously reported by us, and that of phenyl indole-3-thiolobutyrate has been disclosed herein.

4. Phenyl indole-3-thiolobutyrate represents a new structural class of auxin plant growth regulators, and will be particularly useful in inducing root initiation in plant cuttings. Phenyl indole-3-thiolobutyrate may be more effective in inducing rooting of cuttings of species other than the bioassay species, i.e. bean and jack pine.

5. Other thioesters of indolealkanoic acids may also exist that promote root initiation as or more effectively than phenyl indole-3-thiolobutyrate.

The foregoing description of the specific embodiments will so fully reveal the general nature of the invention that others of ordinary skill in the art can by applying current knowledge, readily modify and/or

TABLE 2

Effect the indole-3-butyric acid and phenyl indole-3-thiolbutyrate on adventitious root initiation and elongation in 60-day-old jack pine seedling cuttings after 3 weeks propagation. Cuttings were treated by touching the cut basal surface to undiluted, powdered, crystalline chemical before being placed into the propagation bed. Data are means based on 20 values from one replication of the experiment in time. An asterisk in the column below a mean indicates that the mean below which the asterisk appears differed significantly (Pr >0.05) from the treatment mean in the row where the asterisk appears. Statistical comparisons are based on a Mann-Whitney U-test.

| Treatment | | No. roots per cutting by treatment no. | | | % rooted | % with 1 cm or more dead basal stem | Length (mm) longest root per cutting by treatment no. | | |
|---|---|---|---|---|---|---|---|---|---|
| No. | Name | (1) | (2) | (3) | | | (1) | (2) | (3) |
| (1) | Control | 0.5 | | | 25 | 0 | 0.4 | | |
| (2) | IBA | | 1.0 | | 15 | 85 | | 2.2 | |
| (3) | P-ITB | * | * | 3.0 | 80 | 0 | * | * | 4.6 |

Abbreviations:
IBA—indole-3-butyric acid;
P-ITB—phenyl indole-3-thiolobutyrate adapt for various applications such specific embodiments without departing from the generic concept, and therefore, such adaptations and modifications should and are intended to be comprehended within the meaning and range of equivalents of the disclosed embodiments. It is understood that the phraseology or terminology employed herein is used for the purpose of description and not of limitation.

What is claimed is:

1. A synthetic auxin composition for stimulating adventitious root formation in difficult-to-root cuttings, comprising an amount sufficient to stimulate adventitious root formation of a compound or mixture of compounds selected from the group consisting of phenyl indole-3-thiol lower alkylene esters wherein the alkylene ester group has up to 4 carbons; and a volatile or inert non-toxic carrier.

2. An improved synthetic auxin composition according to claim 1, wherein said compound or mixture of compounds is selected from the group consisting of phenyl indole-3-thiolacetate and phenyl indole-3-thiolobutyrate.

3. A composition according to claim 1, wherein said compound is phenyl indole-3-thiolobutyrate.

4. A method of stimulating adventitious root formation of plant cuttings comprising contacting the stem of a plant cutting with a phenyl indole-3-thiol lower alkylene ester wherein the alkylene ester group has up to 4 carbons or a mixture thereof; and maintaining said cutting in an environment for developing roots on the stem of said cutting until the roots develop to an extent that said cutting is suitable for transplanting.

* * * * *